(12) United States Patent
Durfee

(10) Patent No.: US 10,881,757 B2
(45) Date of Patent: Jan. 5, 2021

(54) PLASMA AIR PURIFIER

(71) Applicant: Creatrix Solutions LLC, Kennewick, WA (US)

(72) Inventor: Eileen Durfee, Kennewick, WA (US)

(73) Assignee: CREATRIX SOLUTIONS LLC, Kennewick, WA (US)

( * ) Notice: Subject to any disclaimer, the term of this patent is extended or adjusted under 35 U.S.C. 154(b) by 430 days.

(21) Appl. No.: 15/868,650

(22) Filed: Jan. 11, 2018

(65) Prior Publication Data

US 2018/0133356 A1 May 17, 2018

Related U.S. Application Data

(63) Continuation-in-part of application No. PCT/US2015/041644, filed on Jul. 23, 2015.

(Continued)

(51) Int. Cl.
*A61L 9/22* (2006.01)
*B01D 53/32* (2006.01)
(Continued)

(52) U.S. Cl.
CPC .............. *A61L 9/22* (2013.01); *B01D 53/32* (2013.01); *B01D 53/323* (2013.01); *B01D 53/44* (2013.01); *B01D 53/52* (2013.01); *B01D 53/58* (2013.01); *A61L 2209/11* (2013.01); *A61L 2209/212* (2013.01); *B01D 2257/708* (2013.01); *B01D 2257/90* (2013.01); *B01D 2257/91* (2013.01); *B01D 2258/06* (2013.01);

(Continued)

(58) Field of Classification Search
CPC .. A61L 9/22; A61L 2209/212; A61L 2209/11; B01D 53/323; B01D 53/58; B01D 53/52; B01D 53/44; B01D 53/32; B01D 2257/708; B01D 2257/91; B01D 2257/90; B01D 2258/06; B01D 2259/818; H05H 2001/483; H05H 2245/121

See application file for complete search history.

(56) References Cited

U.S. PATENT DOCUMENTS

| 7,537,647 | B2 * | 5/2009 | Adair ..................... | B01D 45/06 |
| | | | | 261/DIG. 88 |
| 2005/0082160 | A1 * | 4/2005 | Botvinnik ................ | B03C 3/49 |
| | | | | 204/164 |

(Continued)

*Primary Examiner* — Regina M Yoo

(57) ABSTRACT

The plasma air purifier is an apparatus that simultaneously produces positive ions and negative ions in order to eliminate bacteria, viruses and odors in the air of the surrounding environment. The apparatus includes a housing, a discharge plate, a discharge needle array, a microcontroller, and a power supply. The housing encloses the discharge needle array, the microcontroller, and the power supply, allowing the apparatus to be easily incorporated into a variety of environments and easily transported. The discharge plate is mounted onto the housing via at least one first pillar and at least one second pillar. The discharge plate produces negative ions, and the discharge needle array produces positive ions. The discharge needle array is electronically connected to the microcontroller. The power supply is electrically connected to the microcontroller and the discharge plate. The discharge needle array is electrically connected to the power supply through the microcontroller.

20 Claims, 12 Drawing Sheets

Related U.S. Application Data

(60) Provisional application No. 62/193,887, filed on Jul. 17, 2015.

(51) Int. Cl.
*B01D 53/44* (2006.01)
*B01D 53/52* (2006.01)
*B01D 53/58* (2006.01)
H05H 1/48 (2006.01)

(52) U.S. Cl.
CPC . *B01D 2259/818* (2013.01); *H05H 2001/483* (2013.01); *H05H 2245/121* (2013.01)

(56) References Cited

U.S. PATENT DOCUMENTS

| | | | |
|---|---|---|---|
| 2008/0130190 A1* | 6/2008 | Shimada | H01T 23/00 361/231 |
| 2013/0258543 A1* | 10/2013 | Suzuki | H01T 23/00 361/231 |

* cited by examiner

PLASMA AIR PURIFIER

The current application is a continuation-in-part (CIP) application of the Patent Cooperation Treaty (PCT) application PCT/US2015/41644 filed on Jul. 23, 2015. The PCT application PCT/US2015/41644 claims a priority to the U.S. Provisional Patent application Ser. No. 62/193,887 filed on Jul. 17, 2015.

FIELD OF THE INVENTION

The present invention generally relates to air purifiers. More specifically, the present invention is a plasma air purifier used to treat air and eliminate volatile organic compounds (VOCs), bacteria, mold, and viruses through the simultaneous production of large amounts of positive and negative ions by utilizing a boosted circuit design.

BACKGROUND OF THE INVENTION

Throughout everyday life, humans are constantly exposed to an abundance of potentially harmful chemicals, including but not limited to Formaldehyde, Acetone, 1,2-Dichloroethane, Trichloroethylene, Tetrachloroethylene, Vinyl Chloride, Benzene, Toluene, Styrene, Dichloromethane, and more. Volatile organic compounds (VOCs) are released gases from particular liquids or solids that are typically found to be much more highly concentrated in indoor settings, rather than outdoor, which negatively impact air quality.

Fortunately, plasma air purifiers have been developed to treat the air and eliminate VOCs. Plasma works as a powerful agent against these compounds and decomposes them in less time than other sources, such as ultraviolet light. Furthermore, the benefits of plasma include enabling oxygen to be more effectively absorbed from ionized air and helping to eliminate odors when both gases and aerosols contact active oxygen molecules.

Plasma forms millions of ions that travel into the air and attacks pollutants. Enormous amounts of energy are released during the neutralization of positive and negative charges, resulting in the change of structure of the surrounding bacteria and bacterial death. Plasma exposure decreases the particle size of metal oxides and purifies the air through the filtration of bacteria and viruses. Active oxygen molecules bond with bacteria and mold, which cannot multiply once oxidized and destroyed. Current plasma air purifiers produce positive and negative ions in a continuous and alternating fashion in lower concentrations. However, there exists a need for a portable and inexpensive plasma air purifier that produces both positive and negative ions into the air in higher concentrations for greater effectiveness.

It is therefore an objective of the present invention to introduce a new plasma air purifier. The present invention works under graphite point discharge, which is produced through independent tiny units of oxygen molecules, leading to the formation of ozone integration strings that quickly breakdown during the air purification process. Since ozone integration strings dissipate so quickly, the ambient air levels of ozone never exceed safe allowable limits, even when the present invention is used in small spaces (e.g. automobiles).

The present invention generates a large number of small ion clusters while in an electric field that is preferably more than 10 kV. These small ions collide with oxygen molecules in the air to produce positive and negative oxygen ions. Due to increased potency, positive oxygen ions oxidize and decompose methyl mercaptan, ammonia, hydrogen sulfide, and other pollutants in very short amounts of time and, as well as, stimulate the chemical reaction of volatile organic gases. After a series of reactions, carbon and water are ultimately generated. Positive ions also destroy the living conditions of active bacteria in the air, inactive bacteria, and spores. Thus, the reproduction of these organisms is disabled and the concentration of bacteria in the surrounding environment is reduced. Moreover, the production of negative oxygen ions is essential as they may absorb suspended particles weighing dozens of times greater than itself and descent gravity. With this, suspended colloids (aerosols) are removed and the air is purified when the present invention is in use.

The present invention emits large quantities of ions, which come in contact with bacteria, viruses, or mold spores. The ions are transformed into Hydroxide (OH) radicals and the oxidation that occurs is powerful, causing OH radicals to break down the protein surface by repeatedly stealing hydrogen (H) atoms from the organism's surface. Bacteria, viruses, and mold spores cannot mutate to become resistant to this process and in this way a bacterial, anti-viral, and anti-fungal effect is achieved. Overall, the present invention is lightweight, portable, sturdy, durable, easy to use, safe, and effective. The present invention has overcome the disadvantages of corona discharge plasma generators and similar plasma generating air purifiers. The present invention produces little to no audible noise. The present invention does not have power loss, insulation damage of devices, purple glow, and static electricity discharge.

DETAIL DESCRIPTIONS OF THE INVENTION

Figure 1:
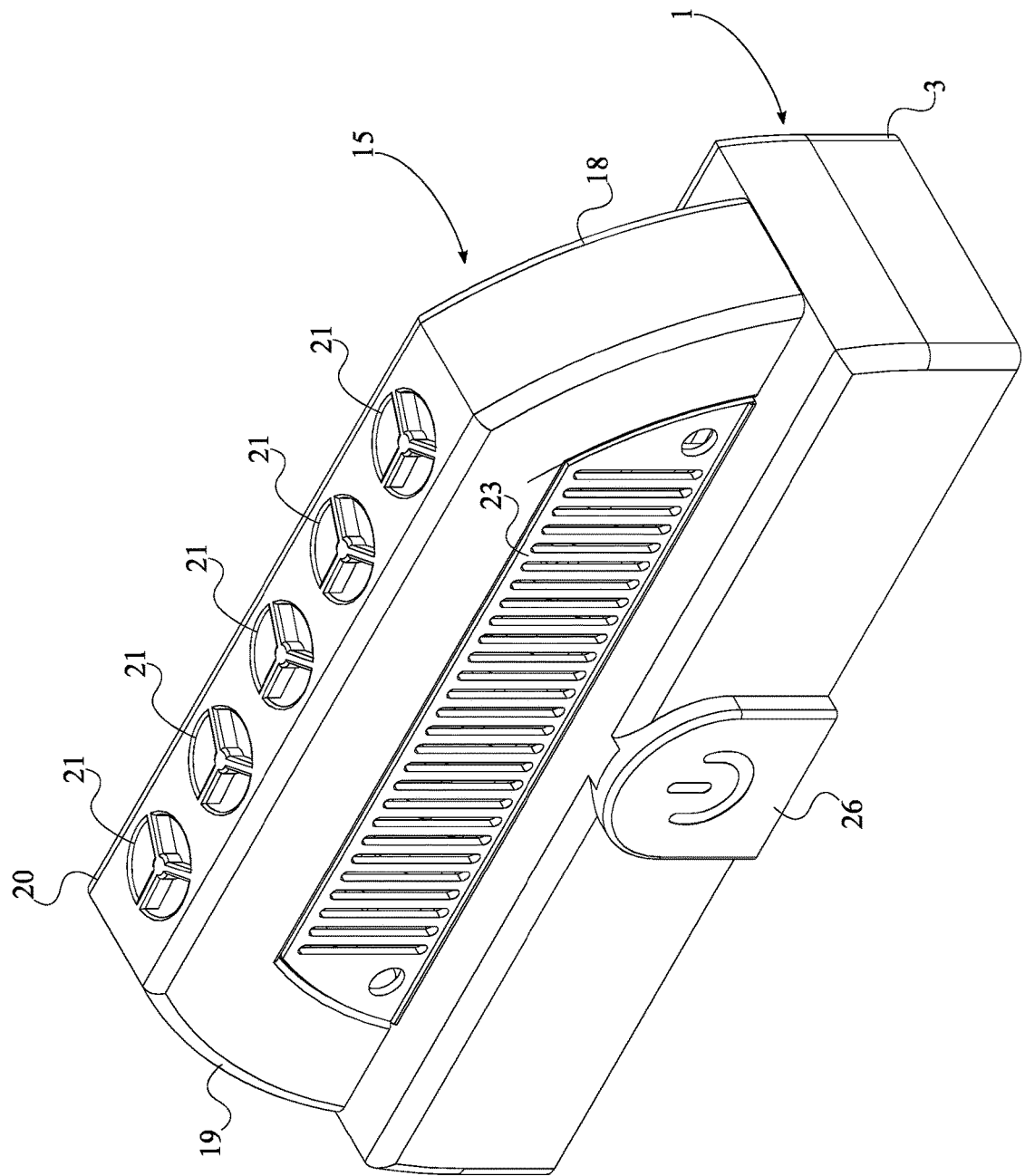
FIG. 1 is a front perspective view of the preferred embodiment of the present invention with the first ventilated grill and the second ventilated grill.
Figure 2:
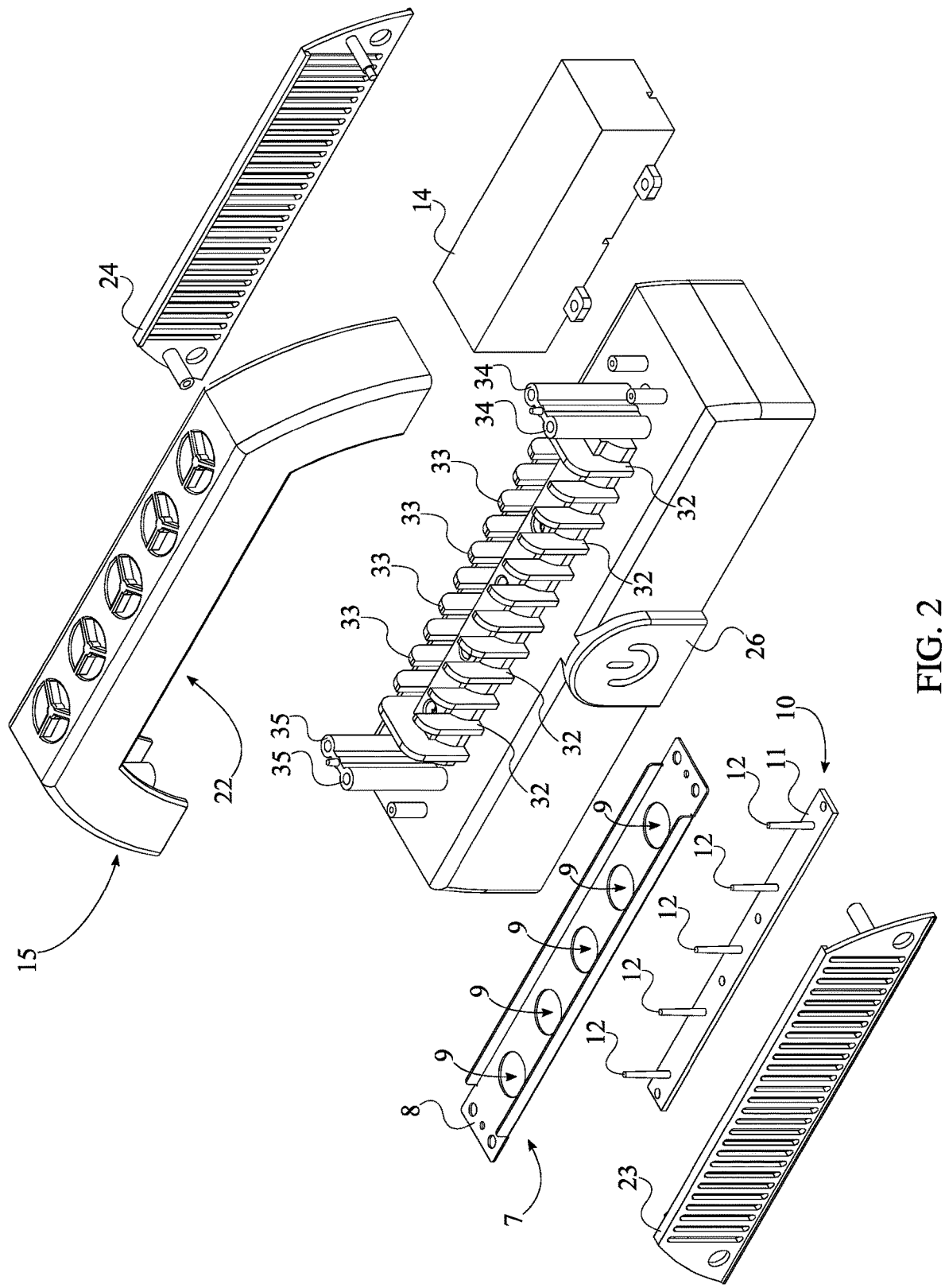
FIG. 2 is an exploded view of the preferred embodiment of the present invention.
Figure 3:
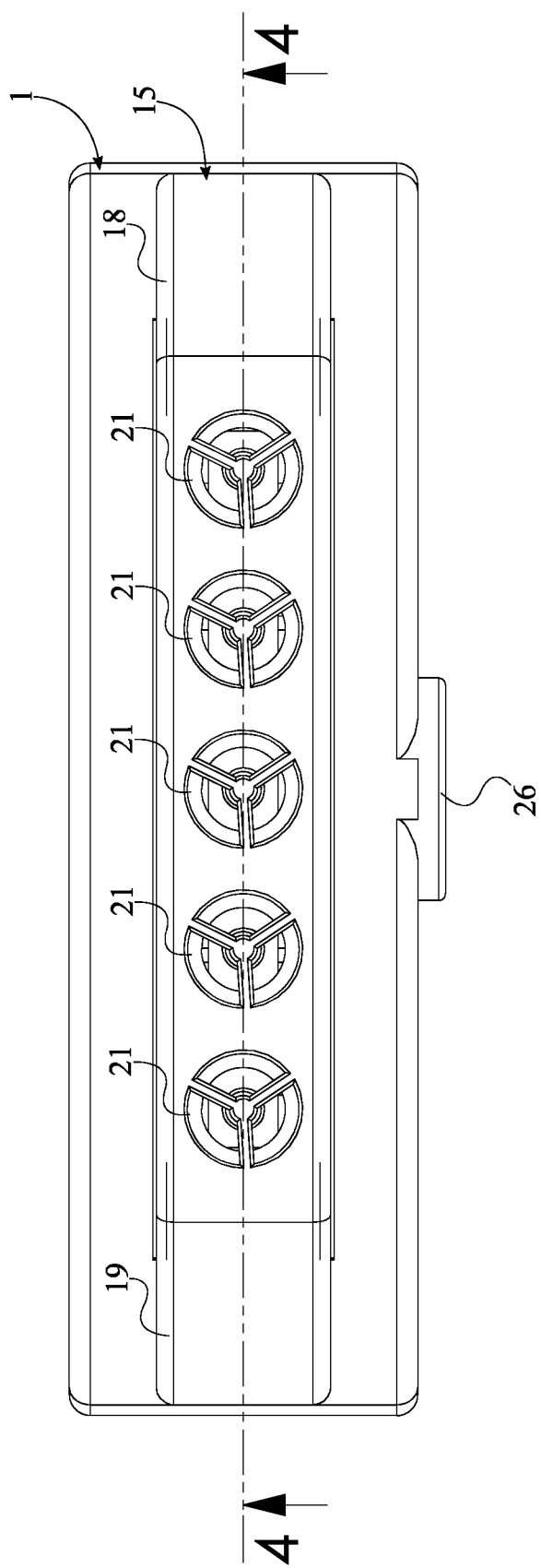
FIG. 3 is a top side view of the preferred embodiment of the present invention.
Figure 4:
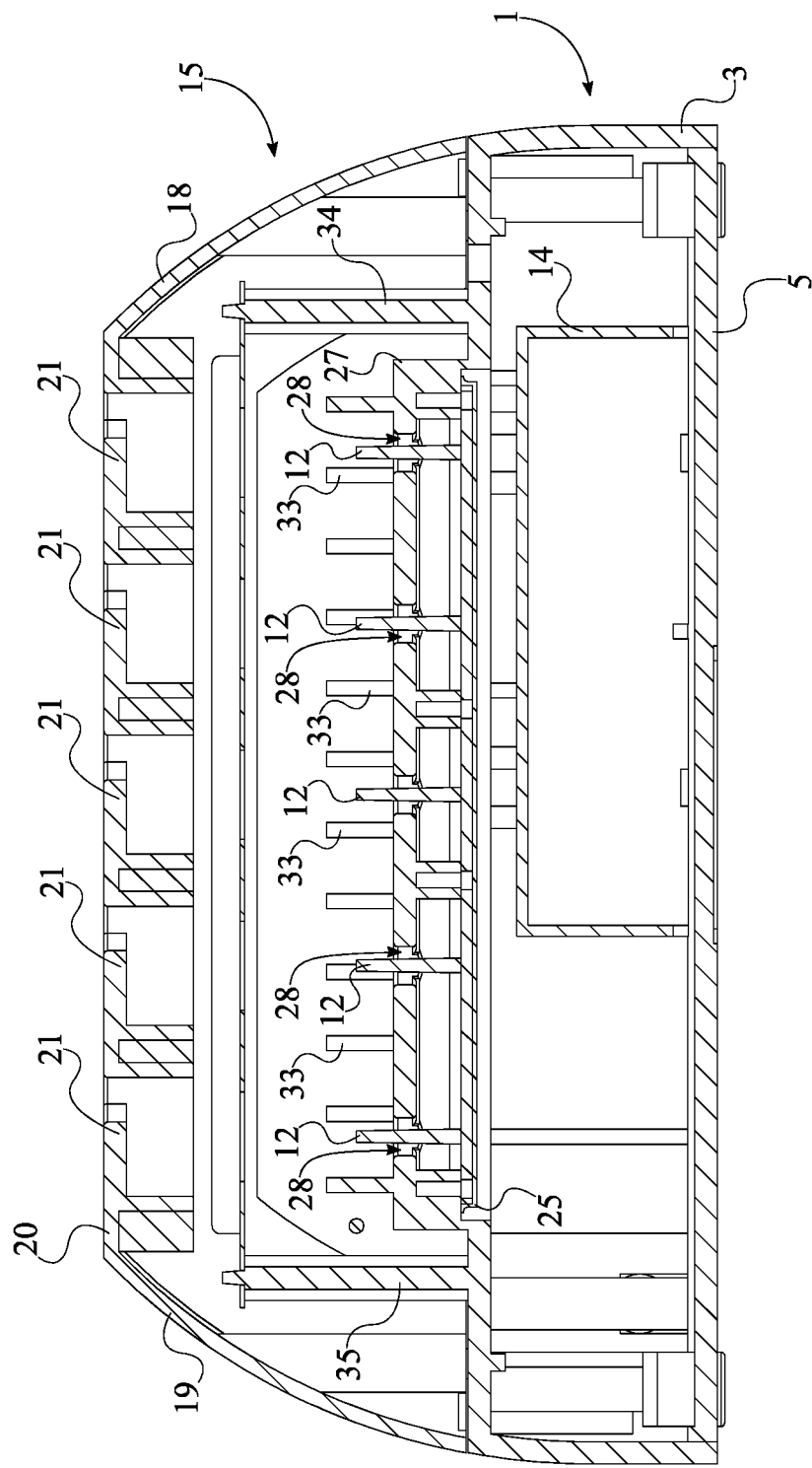
FIG. 4 is a cross-sectional view of FIG. 3 along line 4-4 of the preferred embodiment of the present invention.
Figure 5:
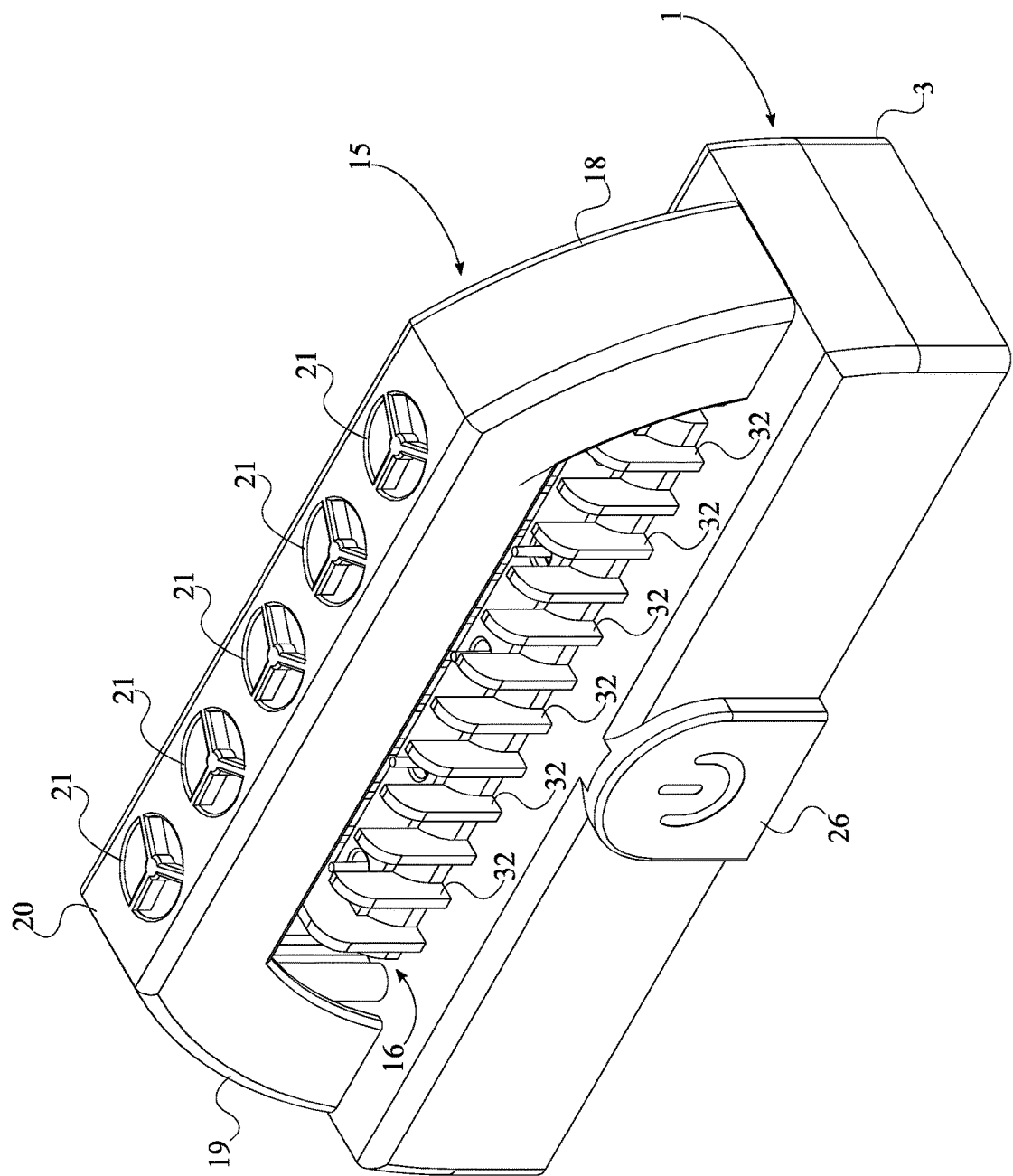
FIG. 5 is a front perspective view of the preferred embodiment of the present invention.
Figure 6:
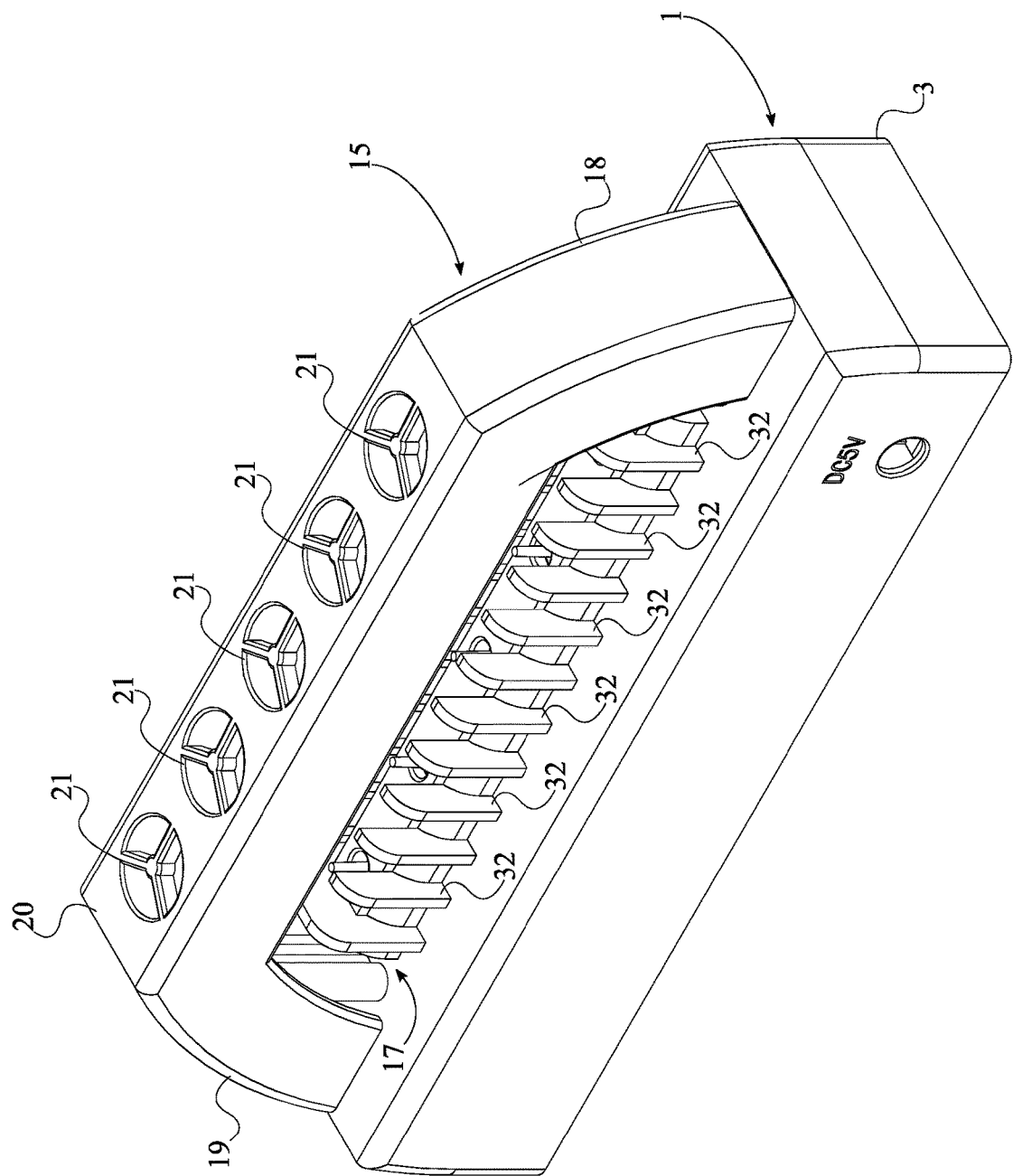
FIG. 6 is a rear perspective view of the preferred embodiment of the present invention.
Figure 7:
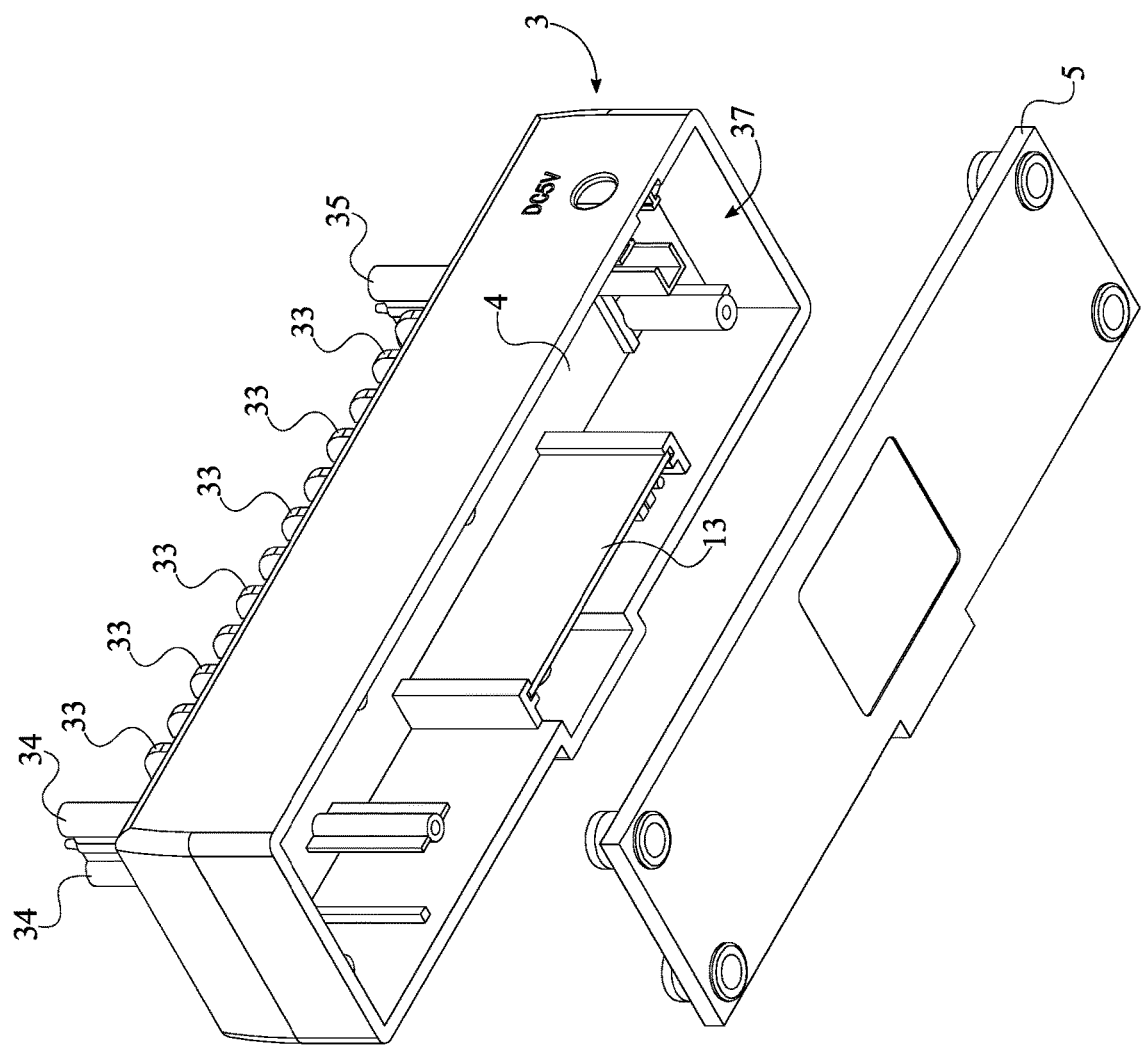
FIG. 7 is a rear exploded view of the present invention without the cover.
Figure 8:
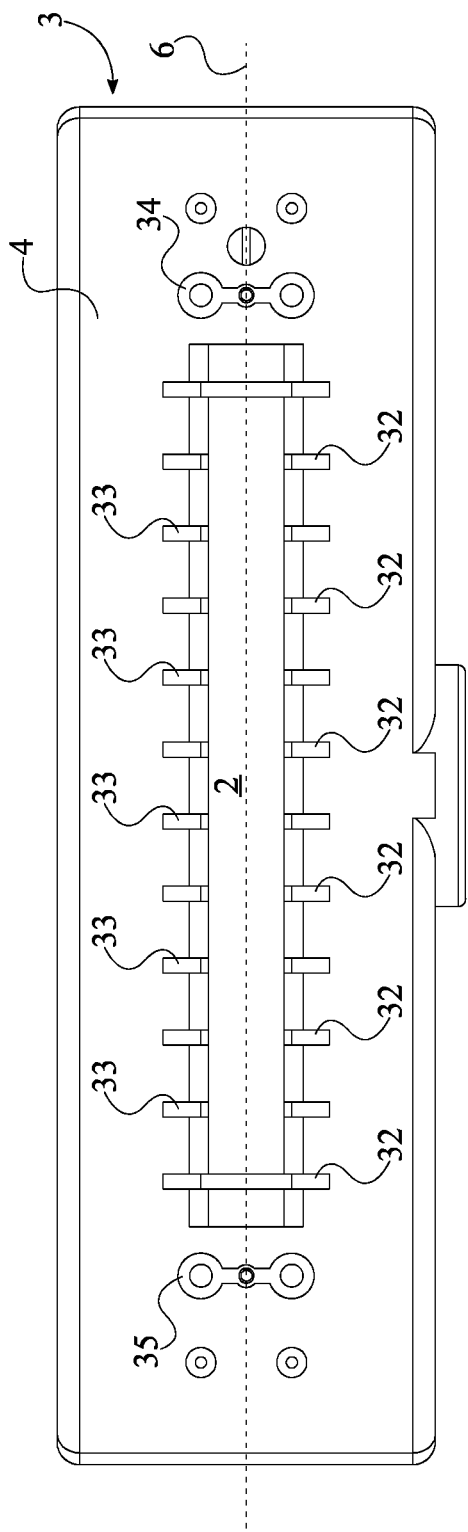
FIG. 8 is a top side view of the present invention without the cover, the slot-covering plate, and the plurality of needle holes.
Figure 9:
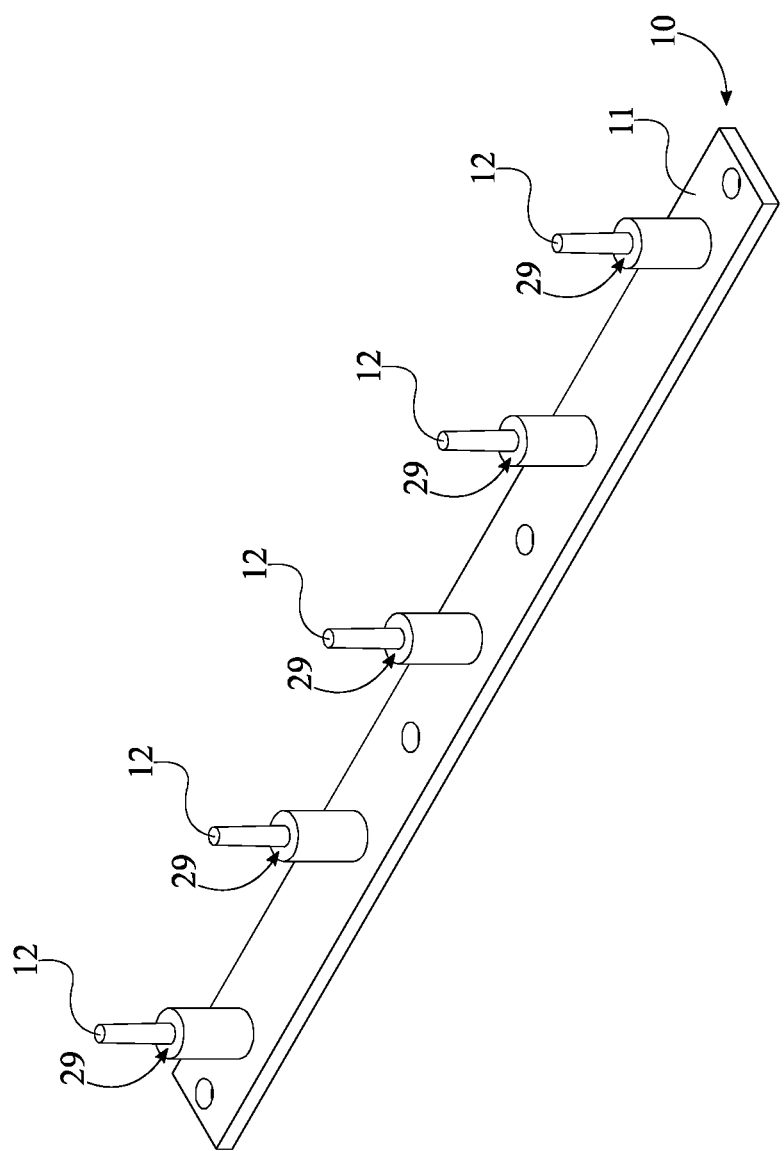
FIG. 9 is a front perspective view of the discharge needle array of the present invention.
Figure 10:
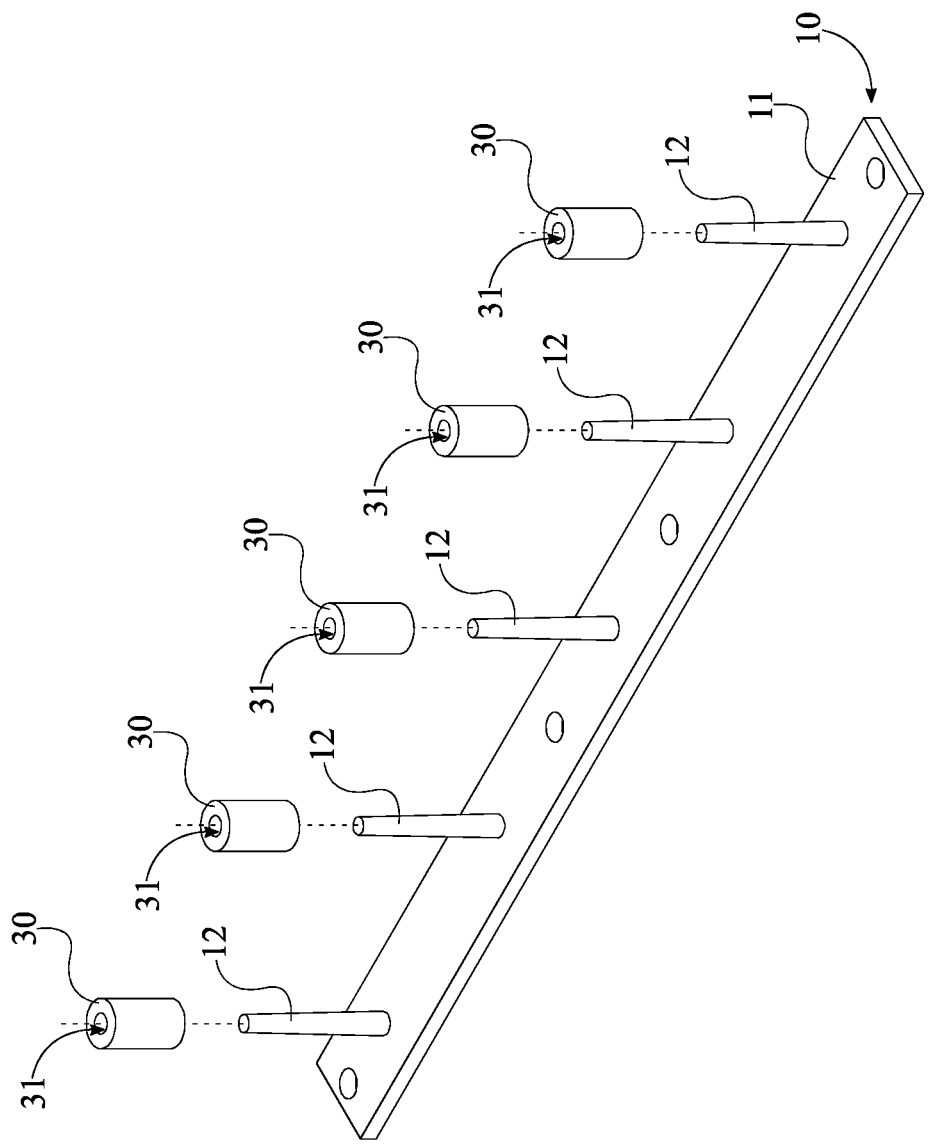
FIG. 10 is an exploded view of the discharge needle array of the present invention.
Figure 11:
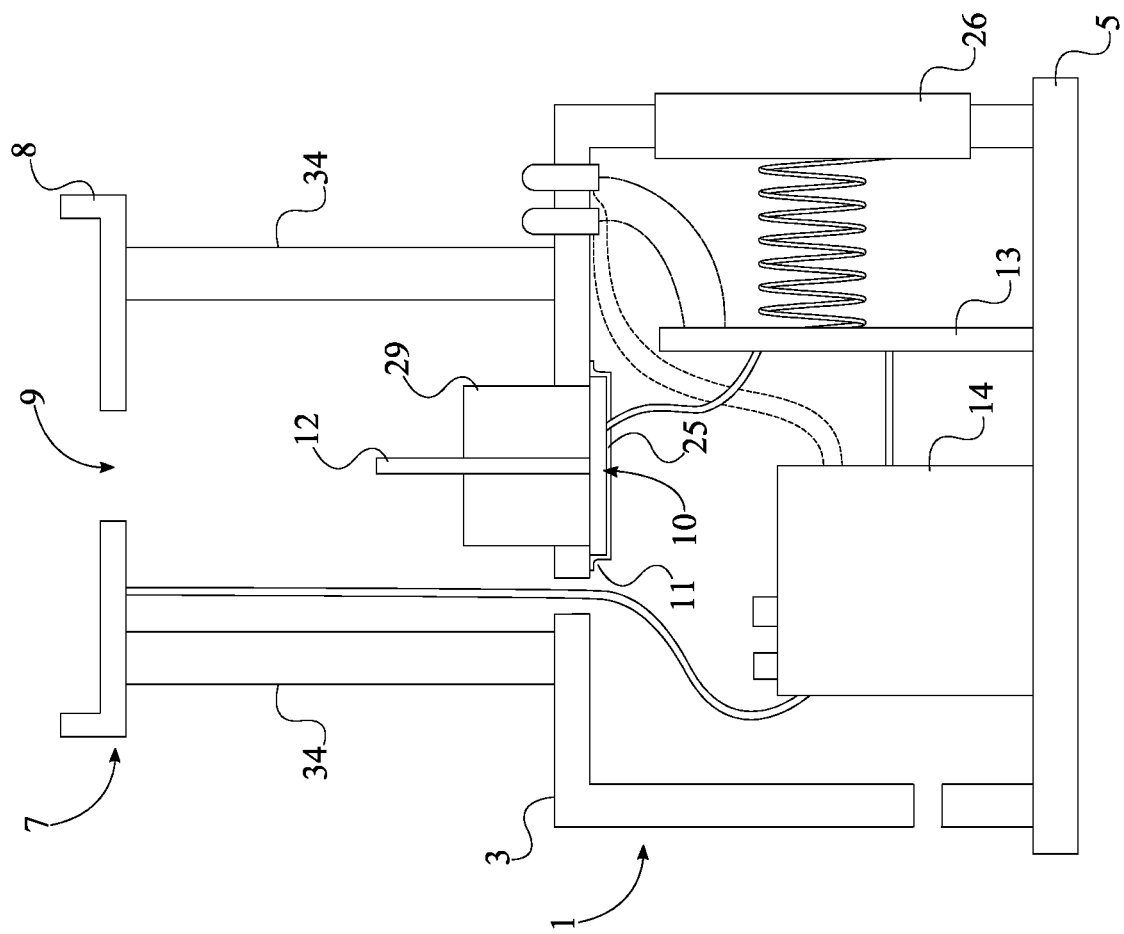
FIG. 11 is a schematic view of the electronic connections of the present invention.
Figure 12:
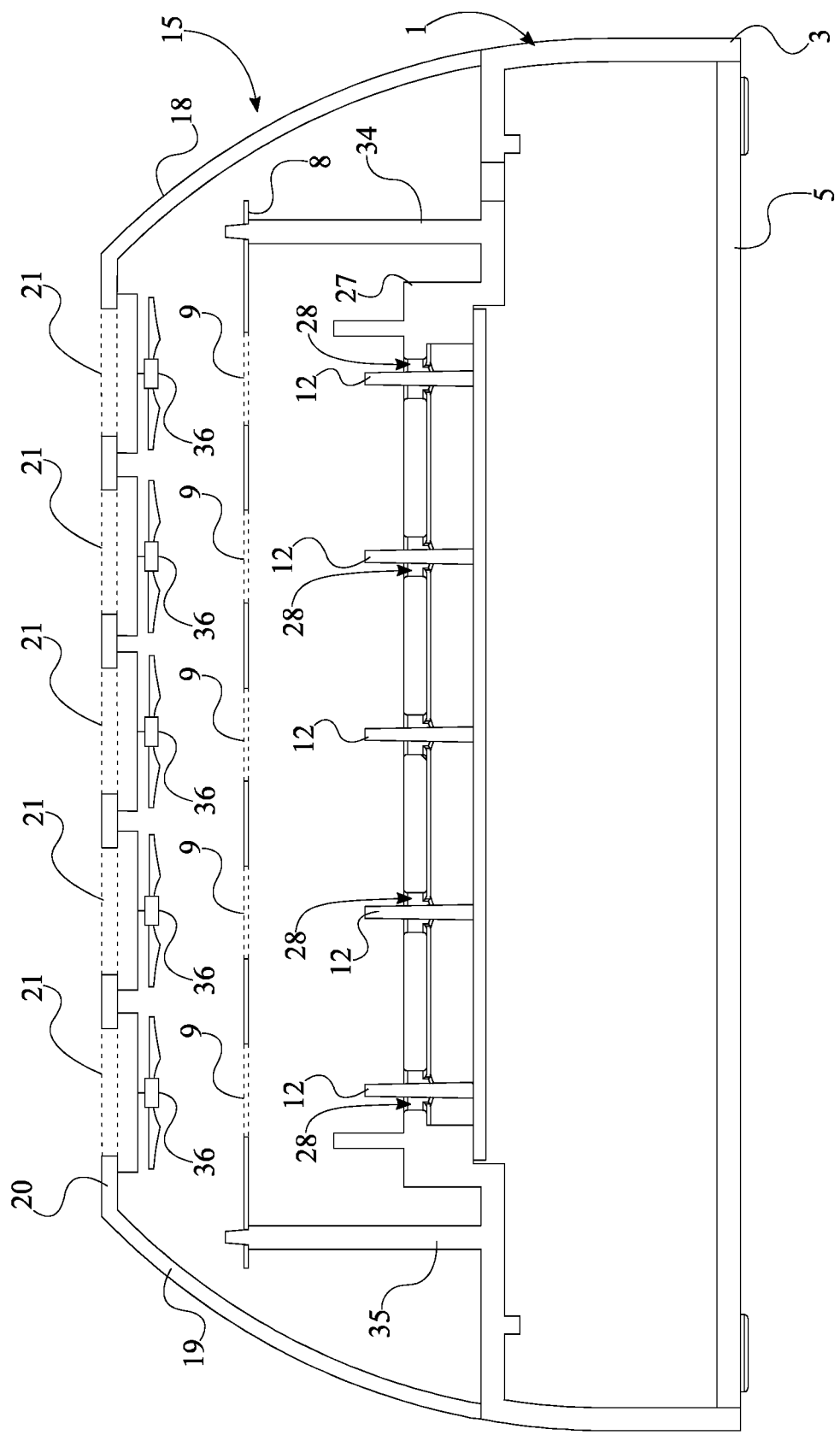
FIG. 12 is a schematic view of an alternate embodiment of the present invention with a plurality of fans.

All illustrations of the drawings are for the purpose of describing selected versions of the present invention and are not intended to limit the scope of the present invention.

The present invention is a plasma air purifier that eliminates impurities in the air through the production of positive ions and negative ions simultaneously. The present invention is portable and compact so that the present invention may be integrated into a variety of environments. The present invention comprises a housing 1, a discharge plate 7, a discharge needle array 10, a microcontroller 13, and a power supply 14. The housing 1 contains the discharge needle array 10, the microcontroller 13, and the power supply 14. Moreover, the housing 1 positions the discharge plate 7 and the discharge needle array 10, thereby facilitating the emission of positive ions and negative ions. The discharge plate 7, in conjunction with the power supply 14, produces negative ions. The discharge needle array 10, in conjunction with the main circuit board, produces positive ions. The discharge needle array 10 comprises a base plate 11 and a plurality of needles 12. The base plate 11 positions and allows for an electrical current from the microcontroller 13 to reach each of the plurality of needles 12, each of which emit positive ions. Both the base plate 11 and the plurality of needles 12 are metallic in order for positive ions to be produced with the application of the electrical current. The microcontroller 13 controls a variety of types of emission of the positive ions and negative ions. Furthermore, the microcontroller 13 controls the electrical current from the power supply 14 to the discharge needle array 10. The power supply 14 provides the necessary power to the microcontroller 13 and the discharge plate 7. The power supply 14 is preferably a portable power supply 14 such as a battery. However, in alternate embodiments of the present invention, the power supply 14 may also be a rechargeable battery or a battery pack that must be connected to an outlet via a power cord.

The overall arrangement of the aforementioned components allows the present invention to effectively distribute positive ions and negative ions. The plurality of needles 12 is distributed across and oriented normal to the base plate 11, thereby maximizing the area of emission of positive ions. Moreover, the base plate 11 is electrically connected to the plurality of needles 12 which allow for the emission of the positive ions through the plurality of needles 12. The base plate 11, the microcontroller 13, and the power supply 14 are positioned within the housing 1, containing and positioning loose components and allowing the present invention to be portable. In order to distance the discharge plate 7 and the discharge needle array 10 from each other and eliminate a hazardous environment with the electrically charged discharge plate 7 and the discharge needle array 10, the discharge plate 7 is mounted onto the housing 1. The plurality of needles 12 traverses out of a slot 2 of the housing 1 in order for the positive ions to enter the air of the surrounding environment. More specifically, the plurality of needles 12 and the discharge plate 7 are positioned offset from each other by an arcing distance, thereby creating an electric field with the emissions of positive and negative ions.

In order for positive ions to be produced, the discharge needle array 10 is electronically connected to the microcontroller 13. The discharge needle array 10 and the discharge plate 7 each receives an electrical current as the power supply 14 is electrically connected to the microcontroller 13 and the discharge plate 7, respectively. More specifically, the discharge needle array 10 is electrically connected to the power supply 14 through the microcontroller 13. The microcontroller 13 and the power supply 14 boost 5-12 direct current (DC) volts (V) to 10 kilovolts (kV) of positive and negative voltage through a frequency-conversion circuit. The air is ionized under an electrical field of the positive and negative voltage, generated with the discharge needle array 10 and the discharge plate 7. This ionization results with a large number of positive ions and negative ions produced and emitted into the surrounding environment. A stronger electric field of negative voltage is present, resulting in more negative ions and a powerful air purifier. Negative ions that remain in the air after neutralization remove dust, smoke, odors, and so on, thereby improving overall air quality of the surrounding environment of the present invention.

The present invention allows the positive ions and the negative ions to freely move through the air of the surrounding environment while protecting a user or users from the plurality of needles 12 as the present invention further comprises a cover 15 and a main ventilation hole 22. The cover 15 prevents the hands and fingers of a user from coming into contact with the plurality of needles 12. The cover 15 also allows the user to grasp onto the present invention and move the present invention as necessary. The main ventilation hole 22 allows the positive ions and the negative ions to be freely distributed to the surrounding environment. The cover 15 is mounted onto the housing 1 in order to surround the plurality of needles 12 as well as the discharge plate 7. In the preferred embodiment of the present invention, the housing 1 comprises at least one first pin and at least one second pin that traverse into at least one first slot and at least one second slot of the cover 15, respectively. The at least one first pin and the at least one second pin are mounted onto the housing 1, and the slot 2 of the housing 1 is positioned in between the at least one first pin and the at least one second pin. The at least one first slot and the at least one second slot are integrated into the cover 15 and are positioned opposite each other about the cover 15. The main ventilation hole 22 traverses through the cover 15 and is positioned adjacent to the housing 1, thereby maximizing the emission of positive ions and negative ions. More specifically, the discharge plate 7 is positioned in between the base plate 11 and the cover 15 and the main ventilation hole 22 is in fluid communication with the plurality of needles 12.

In an alternate embodiment of the present invention, the attachment of the cover 15 with the housing 1 allows the present invention to be stackable with an arbitrary housing 1 and a corresponding cover 15. This alternate embodiment allows a user to connect a plurality of housings and covers in order to increase the amounts of positive ions and negative ions within a given environment.

In order to further enhance the safety of the present invention, the preferred embodiment of the present invention comprises a first ventilated grill 23 and a second ventilated grill 24. Furthermore, the cover 15 comprises a first opening 16 and a second opening 17. The first ventilated grill 23 and the second ventilated grill 24 prevent the hands or fingers of the user from slipping through the first opening 16 and the second opening 17, respectively, and coming into contact with the plurality of needles 12. The first opening 16 and the second opening 17 allows for the positive ions and the negative ions to the air of the surrounding environment. The first opening 16 and the second opening 17 are positioned opposite each other along the main ventilation hole 22, facilitating the path of the positive ions and the negative ions into the air of the surrounding environment. The first ventilated grill 23 is mounted across the first opening 16. Similarly, the second ventilated grill 24 is mounted across the second opening 17. This arrangement protects the user from coming into contact with the plurality of needles 12 without inhibiting the natural path of positive and negative ions from the present invention into the air of the surrounding environment.

The present invention effectively positions and contains the discharge needle array 10, the microcontroller 13, and the power supply 14 as the housing 1 further comprises a receptacle 3 and a covering plate 5. The receptacle 3 surrounds the aforementioned components and the covering plate 5 encloses the aforementioned components within the receptacle 3. A base 4 of the receptacle 3 is positioned adjacent to the cover 15. Consequently, an opening 37 of the receptacle 3 is positioned opposite the base 4 of the receptacle 3. The slot 2 traverses through the base 4 of the receptacle 3, and the plurality of needles 12 is positioned through the slot 2. This arrangement allows the positive ions to freely enter the air of the surrounding environment. The base plate 11 is connected across the base 4 of the receptacle 3 in order for the plurality of needles 12 to traverse out of the slot 2. In the preferred embodiment of the present invention, the base plate 11 is fastened to the base 4 of the receptacle 3 with a plurality of screws which traverse through the base plate 11 and into the base 4 of the receptacle 3. The covering plate 5 is detachably attached across the opening 37 of the receptacle 3 so that the discharge needle array 10, the microcontroller 13, and the power supply 14 are accessible. In order to accommodate for the overall structure of the present invention, the power supply 14 is mounted onto the covering plate 5, which preferably presses against the ground or a comparable resting surface such as a table.

Similar to the preferred embodiment of the housing 1 and the cover 15, the receptacle the receptacle 3 comprises plurality of pins that traverse into a plurality of slots of the covering plate 5. The plurality of pins is mounted within the receptacle 3 and is perimetrically distributed around the base 4 of the receptacle 3. The plurality of slots is integrated into the covering plate 5 and is positioned adjacent the receptacle 3. The plurality of slots is perimetrically distributed around the covering plate 5. Each of the plurality of slots is concentric with a corresponding pin of the plurality of pins. The plurality of pins traverse into the plurality of slots and the covering plate 5 is fastened to the receptacle 3.

The preferred embodiment of the present invention preferably comprises a strip of static tape 25. The strip of static tape 25 reinforces the connection between the base plate 11 of the discharge needle array 10 to the base 4 receptacle 3. More specifically, the base plate 11 is adhered across the base 4 of the receptacle 3 by the strip of static tape 25. This connection allows the discharge needle array 10 to be accessible and interchangeable as necessary.

In order to control the emission of positive and negative ions, the preferred embodiment of the present invention preferably comprises a pressure-sensitive button 26. The pressure-sensitive button 26 is integrated into the receptacle 3 and is positioned in between the base 4 of the receptacle 3 and the opening 37 of the receptacle 3. This arrangement allows the user to easily access the pressure-sensitive button 26. In order to preserve the portable and compact nature of present invention, the microcontroller 13 is mounted within the receptacle 3. This arrangement allows the pressure-sensitive button 26 to be directly connected to the microcontroller 13. More specifically, the pressure-sensitive button 26 is electronically connected to the microcontroller 13, thereby allowing the user to control the types of emission of the positive ions and the negative ions. As the user engages the pressure-sensitive button 26, a visual indicator may alert the user of each type of emission. The visual indicator is preferably externally mounted onto the housing 1, and is electronically connected to the microcontroller 13.

The preferred embodiment of the present invention further comprises a slot-covering plate 27 and a plurality of needle holes 28. The slot-covering plate 27 covers both the slot 2 of the housing 1 and the base plate 11 of the discharge needle array 10, preventing a user from coming into contact with the electrically charged base plate 11. The plurality of needle holes 28 allows the plurality of needles 12 to traverse through the slot-covering plate 27. The slot-covering plate 27 is externally attached onto the base 4 of the receptacle 3 and is positioned along the slot 2 so that the base plate 11 may be effectively connected and adhered across the base 4 of the receptacle 3. The plurality of needle holes 28 traverses through the slot-covering plate 27 and is distributed along the slot-covering plate 27, thereby accommodating the arrangement of the plurality of needles 12 across the base plate 11. More specifically, each of the plurality of needles 12 traverses through a corresponding needle hole from the plurality of needle holes 28 in order for positive ions emitted from the plurality of needles 12 to be released into the air of the surrounding environment.

The preferred embodiment of the present invention further comprises a plurality of electrically-insulative spacers 29 in order to better secure the plurality of needles 12 within the plurality of needle holes 28 and protect the structural integrity of the slot-covering plate 27. Each of the plurality of electrically-insulative spacers 29 comprises a cylindrical body 30 and a channel 31. The cylindrical body 30 secures a corresponding needle of the plurality of needles 12 within a corresponding needle hole of the plurality of needle holes 28 by frictionally engaging with the corresponding needle hole the plurality of needle holes 28. The channel 31 allows the corresponding needle of the plurality of needles 12 to continuously traverse through the cylindrical body 30. Moreover, the channel 31 centrally traverses through the cylindrical body 30. Each of the plurality of needles 12 traverses through the channel 31 of a corresponding spacer from the plurality of electrically-insulative spacers 29. More specifically, the cylindrical body 30 for each of the electrically-insulative spacers 29 traverses through a corresponding needle hole from the plurality of needle holes 28, effectively upholding a corresponding needle of the plurality of needles 12 within the corresponding needle hole of the plurality of needle holes 28.

In order to ensure the safety of the present invention, the preferred embodiment of the present invention comprises an array of first fins 32 and an array of second fins 33. The array of first fins 32 and the array of second fins 33 prevent a finger of the user from coming into contact with the plurality of needles 12 without inhibiting the distribution of positive ions into the air of the surrounding environment. The array of first fins 32 and the array of second fins 33 are externally mounted onto the housing 1 and are distributed along the slot 2 as the plurality of needles 12 traverse out of the slot 2 of the housing 1. The array of first fins 32 is positioned adjacent to the slot 2. Similarly, the array of second fins 33 is positioned adjacent to the slot 2, opposite the array of first fins 32. This arrangement effectively encloses the plurality of needles 12 between the cover 15 and the housing 1. The emission of positive ions from the plurality of needles 12 to the air of the surrounding environment is preserved as the array of first fins 32 is positioned parallel to each other. Similarly, the array of second fins 33 is positioned parallel to each other. More specifically, the array of first fins 32 and the array of second fins 33 are oriented perpendicular to a sagittal plane 6 of the housing 1.

The present invention further comprises at least one first pillar 34 and at least one second pillar 35 so that the plurality of needles 12 and the discharge plate 7 are positioned offset from each other by the arcing distance. In order for the negative ions to be freely dispersed into the surrounding environment, the at least one first pillar 34 and the at least one second pillar 35 are externally connected to the housing 1. The at least one first pillar 34 is terminally positioned to the slot 2. Similarly, the at least one second pillar 35 is terminally positioned to the slot 2, opposite the at least one first pillar 34. This arrangement allows the plurality of needles 12 to freely traverse through the slot 2 of the housing 1. In order for the positive ions from the plurality of needles 12 and the negative ions from the discharge plate 7 to create an electric field, the discharge plate 7 is mounted onto the at least one first pillar 34 and the at least one second pillar 35, opposite to the receptacle 3.

In the preferred embodiment of the invention, the discharge plate 7 comprises an elongated flat body 8 and a plurality of needle-receiving holes 9. The elongated flat body 8 maximizes the emission of negative ions, and the plurality of needle-receiving holes 9 facilitates the distribution of positive ions into the air of the surrounding environment. The plurality of needle-receiving holes 9 is distributed along the elongated flat body 8 and traverses through the elongated flat body 8. In order to effectively create an electric field, each of the plurality of needles 12 traverses through a corresponding hole from the plurality of needle-receiving holes 9.

In the preferred embodiment of the present invention, the cover 15 comprises a first arm 18, a second arm 19, a connecting bar 20, and a plurality of vents 21. The first arm 18 and the second arm 19 uphold the connecting bar 20 above the plurality of needles 12 and the discharge plate 7. The connecting bar 20 shields a user from the plurality of needles 12 and the discharge plate 7. Furthermore, the connecting bar 20 allows the user to grasp onto the present invention. The plurality of vents 21 allows the positive ions and the negative ions to move freely past the cover 15 and into the air of the surrounding environment. The first arm 18 is terminally fixed to the connecting bar 20. Similarly, the second arm 19 is terminally fixed to the connecting bar 20, opposite the first arm 18. This arrangement supports and positions the connecting bar 20 while preserving the arrangement between the plurality of needles 12, the discharge plate 7, and the housing 1. More specifically, the first arm 18 and the second arm 19 are oriented towards the housing 1 and are connected onto the housing 1, opposite the connecting bar 20. In order to shield the plurality of needles 12 and the discharge plate 7, the connecting bar 20 is aligned along the discharge needle array 10. The positive ions and the negative ions traverse past the cover 15 as the plurality of vents 21 is distributed along the connecting bar 20 and traverses through the connecting bar 20. More specifically, each of the plurality of needles 12 is aligned with a corresponding vent from the plurality of vents 21, facilitating the distribution of positive ions, as well as negative ions.

An alternate embodiment of the present invention comprises a plurality of fans 36 which facilitate the dispersion of positive ions and negative ions into the surrounding environment. Each of the plurality of fans 36 are integrated into a corresponding vent from the plurality of vents 21. The microcontroller 13 is electronically connected to each of the plurality of fans 36 so that the plurality of fans 36 turns on and turn off according to the user input via the pressure-sensitive button 26. In order for the plurality of fans 36 to be able to turn on, the power supply 14 is electrically connected to each of the plurality of fans 36.

Although the invention has been explained in relation to its preferred embodiment, it is to be understood that many other possible modifications and variations can be made without departing from the spirit and scope of the invention as hereinafter claimed.

What is claimed is:
1. A plasma air purifier comprises:
a housing;
a discharge plate;
a discharge needle array;
a microcontroller;
a power supply;
the discharge needle array comprises a base plate and a plurality of needles;
the plurality of needles being distributed across and oriented normal to the base plate;
the base plate being electrically connected to the plurality of needles;
the base plate, the microcontroller, and the power supply being positioned within the housing;
the discharge plate being mounted onto the housing;
the plurality of needles traversing out of a slot of the housing;
the plurality of needles and the discharge plate being positioned offset from each other by an arcing distance;
the discharge needle array being electronically connected to the microcontroller;
the power supply being electrically connected to the microcontroller and the discharge plate; and,
the discharge needle array being electrically connected to the power supply through the microcontroller.
2. The plasma air purifier as claimed in claim 1 comprises:
a cover;
a main ventilation hole;
the cover being mounted onto the housing;
the main ventilation hole traversing through the cover;
the main ventilation hole being positioned adjacent to the housing;
the discharge plate being positioned between the base plate and the cover; and,
the main ventilation hole being in fluid communication with plurality of needles.
3. The plasma air purifier as claimed in claim 2 comprises:
a first ventilated grill;
a second ventilated grill;
the cover comprises a first opening and a second opening;
the first opening and the second opening being positioned opposite to each other along the main ventilation hole;
the first ventilated grill being mounted across the first opening; and,
the second ventilated grill being mounted across the second opening.
4. The plasma air purifier as claimed in claim 1 comprises:
the housing further comprises a receptacle and a covering plate;
a base of the receptacle being positioned adjacent to a cover;
an opening of the receptacle being positioned opposite the base of the receptacle;
the slot traversing through the base of the receptacle;
the plurality of needles traversing through the slot;
the base plate being connected across the base of the receptacle;
the covering plate being detachably attached across the opening of the receptacle; and,
the power supply being mounted onto the covering plate.
5. The plasma air purifier as claimed in claim 4 comprises:
a strip of static tape; and, the base plate being adhered across the base of the receptacle by the strip of static tape.

6. The plasma air purifier as claimed in claim 4 comprises:
a pressure-sensitive button;
the pressure-sensitive button being integrated into the receptacle;
the pressure-sensitive button being positioned in between the base of the receptacle and the opening of the receptacle;
the microcontroller being mounted within the receptacle; and,
the pressure-sensitive button being electronically connected to the microcontroller.

7. The plasma air purifier as claimed in claim 4 comprises:
a slot-covering plate;
a plurality of needle holes;
the slot-covering plate being externally attached onto the base of the receptacle;
the slot-covering plate being positioned along the slot;
the plurality of needle holes traversing through the slot-covering plate;
the plurality of needle holes being distributed along the slot-covering plate; and,
each of the plurality of needles traversing through a corresponding needle hole from the plurality of needle holes.

8. The plasma air purifier as claimed in claim 7 comprises:
a plurality of electrically-insulative spacers;
each of the plurality of electrically-insulative spacers comprises a cylindrical body and a channel;
the channel centrally traversing through the cylindrical body;
each of the plurality of needles traversing through the channel of a corresponding spacer from the plurality of electrically-insulative spacers; and,
the cylindrical body for each of the plurality of electrically-insulative spacers traversing through a corresponding needle hole from the plurality of needle holes.

9. The plasma air purifier as claimed in claim 1 comprises:
an array of first fins;
an array of second fins;
the array of first fins and the array of second fins being externally mounted onto the housing;
the array of first fins and the array of second fins being distributed along the slot;
the array of first fins being positioned adjacent to the slot;
the array of second fins being positioned adjacent to the slot, opposite the array of first fins;
the array of first fins being parallel to each other;
the array of second fins being parallel to each other; and,
the array of first fins and the array of second fins being oriented perpendicular to a sagittal plane of the housing.

10. The plasma air purifier as claimed in claim 1 comprises:
at least one first pillar;
at least one second pillar;
the at least one first pillar and the at least one second pillar being externally connected onto the housing;
the at least one first pillar being terminally positioned to the slot;
the at least one second pillar being terminally positioned to the slot, opposite the at least one first pillar; and,
the discharge plate being mounted onto the at least one first pillar and the at least one second pillar, opposite to a receptacle.

11. The plasma air purifier as claimed in claim 1 comprises:
the discharge plate comprises an elongated flat body and a plurality of needle-receiving holes;
the plurality of needle-receiving holes being distributed along the elongated flat body;
the plurality of needle-receiving holes traversing through the elongated flat body; and,
each of the plurality of needles traversing through a corresponding hole from the plurality of needle-receiving holes.

12. The plasma air purifier as claimed in claim 1 comprises:
a cover comprises a first arm, a second arm, a connecting bar, and a plurality of vents;
the first arm being terminally fixed to the connecting bar;
the second arm being terminally fixed to the connecting bar, opposite the first arm;
the first arm and the second arm being oriented towards the housing;
the first arm and the second arm being connected onto the housing, opposite the connecting bar;
the connecting bar being aligned along the discharge needle array;
the plurality of vents being distributed along the connecting bar; and,
the plurality of vents traversing through the connecting bar.

13. The plasma air purifier as claimed in claim 12 comprises:
each of the plurality of needles being aligned with a corresponding vent from the plurality of vents.

14. The plasma air purifier as claimed in claim 12 comprises:
a plurality of fans;
each of the plurality of fans being integrated into a corresponding vent from the plurality of vents;
the microcontroller being electronically connected to each of the plurality of fans; and,
the power supply being electrically connected to the each of the plurality of fans.

15. A plasma air purifier comprises:
a housing;
a discharge plate;
a discharge needle array;
a microcontroller;
a power supply;
the discharge needle array comprises a base plate and a plurality of needles;
the discharge plate comprises an elongated flat body and a plurality of needle-receiving holes;
the plurality of needles being distributed across and oriented normal to the base plate;
the base plate being electrically connected to the plurality of needles;
the base plate, the microcontroller, and the power supply being positioned within the housing;
the discharge plate being mounted onto the housing;
the plurality of needles traversing out of a slot of the housing;
the plurality of needles and the discharge plate being positioned offset from each other by an arcing distance;
the discharge needle array being electronically connected to the microcontroller;
the plurality of needle-receiving holes being distributed along the elongated flat body;

the plurality of needle-receiving holes traversing through the elongated flat body;

each of the plurality of needles traversing through a corresponding hole from the plurality of needle-receiving holes;

the power supply being electrically connected to the microcontroller and the discharge plate; and the discharge needle array being electrically connected to the power supply through the microcontroller.

16. The plasma air purifier as claimed in claim 15 comprises:

a cover;
a main ventilation hole;
a first ventilated grill;
a second ventilated grill;
the cover being mounted onto the housing;
the main ventilation hole traversing through the cover;
the main ventilation hole being positioned adjacent to the housing;
the discharge plate being positioned between the base plate and the cover;
the main ventilation hole being in fluid communication with plurality of needles;
the cover comprises a first opening and a second opening;
the first opening and the second opening being positioned opposite to each other along the main ventilation hole;
the first ventilated grill being mounted across the first opening; and,
the second ventilated grill being mounted across the second opening.

17. The plasma air purifier as claimed in claim 15 comprises:

the housing further comprises a receptacle and a covering plate;
a strip of static tape;
a pressure-sensitive button;
a slot-covering plate;
a plurality of needle holes;
a base of the receptacle being positioned adjacent to a cover;
an opening of the receptacle being positioned opposite the base of the receptacle;
the slot traversing through the base of the receptacle;
the plurality of needles traversing through the slot;
the covering plate being detachably attached across the opening of the receptacle;
the base plate being adhered across the base of the receptacle by the strip of static tape;
the pressure-sensitive button being integrated into the receptacle;
the pressure-sensitive button being positioned in between the base of the receptacle and the opening of the receptacle;
the microcontroller being mounted within the receptacle;
the pressure-sensitive button being electronically connected to the microcontroller;
the power supply being mounted onto the covering plate;
the slot-covering plate being externally attached onto the base of the receptacle;
the slot-covering plate being positioned along the slot;
the plurality of needle holes traversing through the slot-covering plate;
the plurality of needle holes being distributed along the slot-covering plate; and,
each of the plurality of needles traversing through a corresponding needle hole from the plurality of needle holes.

18. The plasma air purifier as claimed in claim 17 comprises:

a plurality of electrically-insulative spacers;
each of the plurality of electrically-insulative spacers comprises a cylindrical body and a channel;
the channel centrally traversing through the cylindrical body;
each of the plurality of needles traversing through the channel of a corresponding spacer from the plurality of electrically-insulative spacers; and
the cylindrical body for each of the plurality of electrically-insulative spacers traversing through a corresponding needle hole from the plurality of needle holes.

19. The plasma air purifier as claimed in claim 15 comprises:

an array of first fins;
an array of second fins;
at least one first pillar;
at least one second pillar;
the array of first fins and the array of second fins being externally mounted onto the housing;
the array of first fins and the array of second fins being distributed along the slot;
the array of first fins being positioned adjacent to the slot;
the array of second fins being positioned adjacent to the slot, opposite the array of first fins;
the array of first fins being parallel to each other;
the array of second fins being parallel to each other;
the array of first fins and the array of second fins being oriented perpendicular to a sagittal plane of the housing;
the at least one first pillar and the at least one second pillar being externally connected onto the housing;
the at least one first pillar being terminally positioned to the slot;
the at least one second pillar being terminally positioned to the slot, opposite the at least one first pillar; and,
the discharge plate being mounted onto the at least one first pillar and the at least one second pillar, opposite to a receptacle.

20. The plasma air purifier as claimed in claim 15 comprises:

a cover comprises a first arm, a second arm, a connecting bar, and a plurality of vents;
a plurality of fans;
the first arm being terminally fixed to the connecting bar;
the second arm being terminally fixed to the connecting bar, opposite the first arm;
the first arm and the second arm being oriented towards the housing;
the first arm and the second arm being connected onto the housing, opposite the connecting bar;
the connecting bar being aligned along the discharge needle array;
the plurality of vents being distributed along the connecting bar;
the plurality of vents traversing through the connecting bar;
each of the plurality of needles being aligned with a corresponding vent from the plurality of vents;
each of the plurality of fans being integrated into a corresponding vent from the plurality of vents;
the microcontroller being electronically connected to each of the plurality of fans; and, the power supply being electrically connected to the each of the plurality of fans.

\* \* \* \* \*